United States Patent
Krishnan et al.

(10) Patent No.: US 10,000,544 B2
(45) Date of Patent: *Jun. 19, 2018

(54) PROCESS FOR PRODUCTION OF INSULIN AND INSULIN ANALOGUES

(71) Applicant: BioGenomics Limited, West Thane, Maharashtra (IN)

(72) Inventors: Archana Krishnan, Maharashtra (IN); Sanjay Sonar, Maharashtra (IN); Damodar Thappa, Maharashtra (IN)

(73) Assignee: BIOGENOMICS LIMITED, West Thane, Maharashtra (IN)

( * ) Notice: Subject to any disclaimer, the term of this patent is extended or adjusted under 35 U.S.C. 154(b) by 10 days.

This patent is subject to a terminal disclaimer.

(21) Appl. No.: 14/908,854

(22) PCT Filed: Jul. 31, 2014

(86) PCT No.: PCT/IN2014/000506
§ 371 (c)(1),
(2) Date: Jan. 29, 2016

(87) PCT Pub. No.: WO2015/015518
PCT Pub. Date: Feb. 5, 2015

(65) Prior Publication Data
US 2016/0168226 A1 Jun. 16, 2016

(30) Foreign Application Priority Data
Jul. 31, 2013 (IN) .......................... 2527/MUM/2013

(51) Int. Cl.
| | | |
|---|---|---|
| *C12P 21/04* | (2006.01) | |
| *C12P 21/06* | (2006.01) | |
| *C12N 15/00* | (2006.01) | |
| *C12N 1/20* | (2006.01) | |
| *C07H 21/04* | (2006.01) | |
| *C07H 21/02* | (2006.01) | |
| *C07K 14/00* | (2006.01) | |
| *C07K 14/62* | (2006.01) | |
| *C12N 15/70* | (2006.01) | |
| *C12N 15/74* | (2006.01) | |
| *C12P 21/02* | (2006.01) | |

(52) U.S. Cl.
CPC .............. *C07K 14/62* (2013.01); *C12N 15/70* (2013.01); *C12N 15/74* (2013.01); *C12P 21/02* (2013.01)

(58) Field of Classification Search
None
See application file for complete search history.

(56) References Cited

FOREIGN PATENT DOCUMENTS

WO 2004/085472 A1 10/2004

OTHER PUBLICATIONS

International Search Report and Written Opinion from International Application No. PCT/IN2014/000506, dated Mar. 5, 2015.
R. V. Tikhonov et al.: "Recombinant human insulin: VIII. Isolation of fusion protein-S-sulfonate, biotechnological precursor of human insulin, from the biomass of transformed *Escherichia coli* cells", Protein Expression and Purification, Academic Press, San Diego, CA, vol. 21, No. 1, Feb. 1, 2001 (Feb. 1, 2001), pp. 176-182, XP002391620.
P. Jonasson et al.: "Single-Step Trypsincleavage of a Fusion Protein to Obtain Human Insulin and it's C Peptide", European Journal of Biochemistry, Wiley-Blackwell Publishing Ltd, GB, vol. 236, No. 2, Mar. 1, 1996 (Mar. 1, 1996), pp. 656-661, XP008071709.
L. Kober et al.: "Optimized Signal Peptides for the Development of High Expressing CHO Cell Lines", Biotechnology and Bioengineering, vol. 110, No. 4, Apr. 17, 2013 (Apr. 17, 2013), pp. 1164-1173, XP055074908.
B. Martoglio et al.: "Signal Sequences: More than Just Greasy Peptides", Trends in Cell Biology, vol. 8, No. 10, Oct. 1, 1998 (Oct. 1, 1998), pp. 410-415, XP055047993.
A. Mukhopadhyay: "Inclusion Bodies and Purification of Proteins in Biologically Active Forms", Advances in Biochemical Engineering/Biotechnology, vol. 56, 1997, pp. 61-109.
J. Q. Chen et al.: "Production of Human Insulin in an *E. coli* System with Met-Lys-Human Proinsulin as the Expressed Precursor", Applied Biochemistry and Biotechnology, vol. 55, 1995, pp. 5-15.

*Primary Examiner* — Yong D Pak
(74) *Attorney, Agent, or Firm* — Coeus Intellectual Property

(57) ABSTRACT

A process for production of insulin or insulin analogs by expression of Insulin or Insulin analogs through an expression vector in a host cell is provided. The expression vector includes a leader peptide of SEQ ID NO 3; a nucleotide sequence encoding an affinity tag linked to C-terminal end or N terminal end of nucleotide sequence of the leader peptide; and a nucleotide sequence encoding for a cleavage site ligated to nucleotide sequence of the leader peptide through nucleotide sequence encoding the affinity tag.

16 Claims, 3 Drawing Sheets

SEQUENCE LISTING

```
<160> NUMBER OF SEQ ID NOS: 3

<210> SEQ ID NO 1
<211> LENGTH: 5605
<212> TYPE: DNA
<213> ORGANISM: Artificial Sequence
<220> FEATURE:
<223> OTHER INFORMATION: Complete Vector construct, includes various
      regulartory sequences, promoter, leader peptide

<400> SEQUENCE: 1
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tccctttagg     180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
```

-continued

```
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttcttccc    840
agacttgttc aacaggccag ccattacgct cgtcatcaaa atcactcgca tcaaccaaac    900
cgttattcat tcgtgattgc gcctgagcga cgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
```

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg gcctgccac cataccccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gcatgggcgc tactggtgtg    5100
```

```
ccgttcagcg gaatggtgag cctccagatg ggtcatcaag gaagcggtag ctcccatcat    5160
catcatcatc acgaattccg ttttgtgaac caacacctgt gcggctcaca cctggtggaa    5220
gctctctacc tagtgtgcgg ggaacgaggc ttcttctaca cacccaagac ccgccgggag    5280
gcagaggacc tgcaggtggg acaagtggag ctgggtggag gcccggggc cgggagtctt    5340 cagcccttgg cactggaggg ttccctgcag aagcgtggca ttgtggaaca atgctgtacc    5400
agcatctgct ccctctacca gctggagaac tactgcaact aactcgagca ccaccaccac    5460
caccactgag atccggctgc taacaaagcc cgaaaggaag ctgagttggc tgctgccacc    5520
gctgagcaat aactagcata accccttggg gcctctaaac gggtcttgag gggttttttg    5580
ctgaaaggag gaactatatc cggat                                          5605

<210> SEQ ID NO 2
<211> LENGTH: 84
<212> TYPE: DNA
<213> ORGANISM: Artificial Sequence
<220> FEATURE:
<223> OTHER INFORMATION: Leader peptide nucleotide sequence

<400> SEQUENCE: 2
atgggcagca gcatgggcgc tactggtgtg ccgttcagcg gaatggtgag cctccagatg    60
ggtcatcaag gaagcggtag ctcc                                           84

<210> SEQ ID NO 3
<211> LENGTH: 28
<212> TYPE: PRT
<213> ORGANISM: Artificial Sequence
<220> FEATURE:
<223> OTHER INFORMATION: Leader peptide

<400> SEQUENCE: 3

Met Gly Ser Ser Met Gly Ala Thr Gly Val Pro Phe Ser Gly Met Val
1               5                   10                  15

Ser Leu Gln Met Gly His Gln Gly Ser Gly Ser Ser
            20                  25
```

PROCESS FOR PRODUCTION OF INSULIN AND INSULIN ANALOGUES

This application is a National Stage Application of International Application No. PCT/IN2014/000506, filed 31 Jul. 2014, which claims benefit of Serial No. 2527/MUM/2013, filed 31 Jul. 2013 in India and which applications are incorporated herein by reference. To the extent appropriate, a claim of priority is made to each of the above disclosed applications.

FIELD OF THE INVENTION

The present invention relates to production of proteins in a host cell, and more particularly to an expression vector for production of insulin or insulin analogues in prokaryotic cells.

DESCRIPTION OF THE RELATED ART

Recombinant DNA (rDNA) technology has been used to clone, express and purify several proteins of therapeutic or other economic value from prokaryotic cells e.g., bacterial cells. The major advantages of producing recombinant proteins in bacterial cells are shorter time to express proteins coupled with lower costs for production of them. The proteins may be produced in bacterial cells either intracellularly as soluble proteins or inclusion bodies, or extracellularly by secretion into periplasm or nutrient media. Despite the wide applications in production of different types of recombinant proteins, the bacterial production of heterologous proteins continues to face major challenges pertaining to low yields or expression of the recombinant protein like Insulin.

Expressing a heterologous gene in a host organism requires a vector that allows stable transformation of the host cells. Traditionally, higher secretion of the proteins, particularly insulin, or higher expression of the heterologous gene in a bacterial host cell is achieved by providing vectors with promoter sequences of the genes that express at higher levels in the bacterial host cell, by providing viral promoters in the vectors, by changing growth conditions, optimising media, by site-directed mutagenesis or by any other known recombinant DNA technique. However, above strategies fail to check following disadvantages associated with production of insulin in bacterial host cells:
  a) Short half-life
  b) High proteolysis
  c) Low inclusion body formation
  d) Presence of N-terminal Methionine residue in proinsulin/insulin obtained as a result of fermentation in bacterial cells.

A method to overcome some of the above disadvantages includes expressing B-chain and A-chain of insulin separately and then combining the B-chain and A-chain to produce a folded insulin molecule. However, this method has further disadvantages since the manufacturing of two separate chains is problematic owing to complicated procedures. Particularly, the reconstitution of the two chains results in a significant decrease in yields.

One of the preferred methods of production of the proteins like insulin is expressing insulin in form of proinsulin, which is precursor to Insulin made in humans and animals and consists of three chains A-C-B or B-C-A. The mature insulin is obtained after cleaving C-chain peptide from the A-C-B chain of the proinsulin. The gene of insulin is expressed as proinsulin inclusion bodies through a vector having a leader peptide attached to DNA sequence of the proinsulin, followed by cleaving of C-chain peptide to obtain regular insulin in unfolded form, and then refolding unfolded insulin to recover its activity and stability. Since the inclusion body is not affected by proteases, they can be accumulated to a high concentration which leads to higher production of inactive recombinant protein such as insulin.

Traditionally, the method of production of insulin includes inserting a proinsulin precursor gene (in B-C-A or A-C-B conformation) into a plasmid containing a gene of a protein having a high stability, in $E.\ coli$, such as βgalactosidase, and the proinsulin fusion protein inclusion bodies are expressed in $E.\ coli$ transformed with the plasmid (Mukhopadhyay A. Adv Biochem Eng Biotechnol. 1997; 56:61-109). The inclusion bodies thus obtained are purified to increase the purity of insulin. Further, the inclusion bodies are dissolved by a treatment with a denaturant and are subjected to sulphonation to minimise formation of wrong disulphide bonding between molecules. Thereafter, the proinsulin fusion protein is treated with cyanogen bromide (CNBr) to cleave methionine residue connecting the leader peptide with proinsulin, which is followed by removal of CNBr and separation of proinsulin that is further purified and refolded with an oxidation and reduction system. Proinsulin is converted into active insulin by removing C-chain between its A-chain and B-chain using trypsin and/or carboxypeptidase B.

The above described process of production of insulin includes complex separation and purification processes that lead to low yield of insulin from relatively higher yield of proinsulin or inclusion bodies comprising proinsulin. Further, the use of toxic substances like CNBr comes with inherent challenge of handling and disposal of toxic substances. In production of insulin, enzymatic cleavages of the leader peptide or unwanted amino acid groups or peptides have also been explored.

Most of the enzymatic cleavage methods currently available for production of insulin require multiple enzymatic cleavage reactions to produce the protein of interest from the fusion protein inclusion bodies. For example, for obtaining Insulin from proinsulin, trypsin and carboxypeptidase are required to cleave off the C-Chain to give insulin. Trypsin is a serine protease that cleaves peptide chains at the carboxyl side of non-terminal amino acids lysine or arginine. Carboxypeptidase B is a metallocarboxypeptidase that cleaves terminal amino acids, lysine or arginine, from C-terminal end. However, when leader sequences are incorporated to increase formation of inclusion bodies, they are cleaved by additional enzymatic reactions as per the cleavage site present in them. This further complicates the purification process.

In other attempts, leader sequence or peptide used to produce proteins either shows a pre-dominantly hydrophilic or hydrophobic property. When leader sequence is hydrophilic, it leads to generation of more soluble proteins which are readily recognised by the proteases leading to low stability of the inclusion bodies. When leader sequence is hydrophobic, it leads to problems pertaining to refolding of proinsulin. In particular example of insulin, almost all leader peptide sequences currently available have arginine as one of their amino acid residues. This results in a number of digested or cleaved sequences upon digestion with Trypsin or Carboxypeptidase B, which complicates downstream purification process.

An attempt at improving insulin production includes expressing methionine-lysine-proinsulin construct in $E.\ coli$ cells (Chen J Q, et al. Appl Biochem Biotechnol. 1995;

55:5-15). This simplifies the purification but the process generates a large amount of by-products when methionine-lysine-proinsulin is cleaved with trypsin and carboxypeptidase B to produce insulin. Another attempt includes use of lysine-arginine linker with a leader peptide attached to proinsulin (Jonasson P, et al. Eur J Biochem. 1996; 236: 656-61). However, this results in expression of a by-product which is an arginine attached to B-chain of insulin. Other attempts at synthesising leader peptides were directed towards production of insulin in yeast cells.

Accordingly, there remains a need for plasmid vectors for production of insulin through bacterial cells which lead to high yield of insulin and are able to convert or translate high production of inclusion bodies to high recovery of insulin by enabling simple purification processes in their downstream processing.

SUMMARY OF THE INVENTION

In view of the foregoing, the embodiments herein, provide a novel expression vector for production of insulin and insulin analogues.

In an aspect, a process for production of insulin or insulin analogues by expression of Insulin or Insulin analogues through an expression vector in a host cell is provided. The expression vector includes a leader peptide of SEQ ID NO 3; a nucleotide sequence encoding an affinity tag linked to C-terminal end or N terminal end of nucleotide sequence of the leader peptide; and a nucleotide sequence encoding for a cleavage site ligated to nucleotide sequence of the leader peptide through nucleotide sequence encoding the affinity tag.

The leader peptide is expressed as a fusion protein; the fusion protein comprising fusion of the leader peptide of SEQ ID NO 3 and Insulin or Insulin analogues and the host cell is bacteria, preferably E. coli. The leader peptide has Methionine at N-terminus, followed by glycine to impart stability to fusion of the heterologous protein and the leader peptide.

Further, in one embodiment, the affinity tag is his-tag and the leader peptide is linked to proinsulin via the cleavage site. In one embodiment, the cleavage site is arginine.

The expression vector further include a nucleotide sequence encoding a multiple cloning site (MCS) in upstream region of the leader peptide; a nucleotide sequence encoding ribosome binding site (RBS) ligated to N-terminus or C-terminus of the leader peptide; a nucleotide sequence encoding a promoter or operator in the downstream of the ribosome binding site; and a nucleotide sequence encoding an antibiotic selection marker in upstream region of the promoter/operator sequence.

In one embodiment, the antibiotic selection marker is kanamycin. The process further includes formation of compound of formula from group consisting of: A-L-Arg-B-A-C, L-A-Arg-B-A-C, L-A-Arg-A-C-B or A-L-Arg-A-C-B in the host cells; wherein A is the affinity tag, L is the leader peptide of SEQ ID NO 3, Arg is arginine, B is B-chain of Proinsulin or Proinsulin analogue, A is A-chain of Proinsulin or Proinsulin Analogue, C is C-chain of Proinsulin or Proinsulin Analogue.

The process further includes digesting the compound of formula A-L-Arg-B-A-C, L-A-Arg-B-A-C, L-A-Arg-A-C-B or A-L-Arg-A-C-B with Trypsin to cleave off the leader peptide with affinity tag and C-chain of proinsulin to obtain molecule of insulin or insulin analogues having B-chain and A-Chain. The expression vector has nucleotide sequence of SEQ ID NO 1.

In another aspect, a process for production of insulin or insulin analogues by expression of Insulin or Insulin analogues through an expression vector in a host cell is provided. The expression vector includes a leader peptide of SEQ ID NO 3; a nucleotide sequence encoding an affinity tag linked to C-terminal end or N terminal end of nucleotide sequence of the leader peptide; a nucleotide sequence encoding for a cleavage site or Restriction Enzyme (RE) site ligated to nucleotide sequence of the leader peptide through nucleotide sequence encoding the affinity tag; a nucleotide sequence encoding a multiple cloning site (MCS) in upstream region of the leader peptide; a nucleotide sequence encoding ribosome binding site (RBS) ligated to N-terminus or C-terminus of the leader peptide; a nucleotide sequence encoding a promoter or operator in the downstream of the ribosome binding site; and a nucleotide sequence encoding an antibiotic selection marker in upstream region of the promoter/operator sequence.

BRIEF DESCRIPTION OF THE DRAWINGS

For a more complete understanding of the embodiments herein, reference should now be made to the embodiments illustrated in greater detail in the accompanying drawings and described below by way of examples.

DETAILED DESCRIPTION OF THE INVENTION

As required, detailed embodiments are disclosed herein; however, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Vector Deposition

The vector pBGBactX is deposited for the patent purposes under Budapest Treaty at the MTCC (Microbial Type of Culture Collection) Chandigarh, India. The deposit was made on Mar. 21, 2013 and accorded deposit number as MTCC 5818. The sequence was characterised using DNA sequencer.

As mentioned, there is a need for plasmid vectors which lead to high yield of insulin and other heterologous proteins through simple purification processes. The embodiments herein provide a plasmid vector having nucleotide sequence listed under SEQ ID NO. 1.

Figure 1:
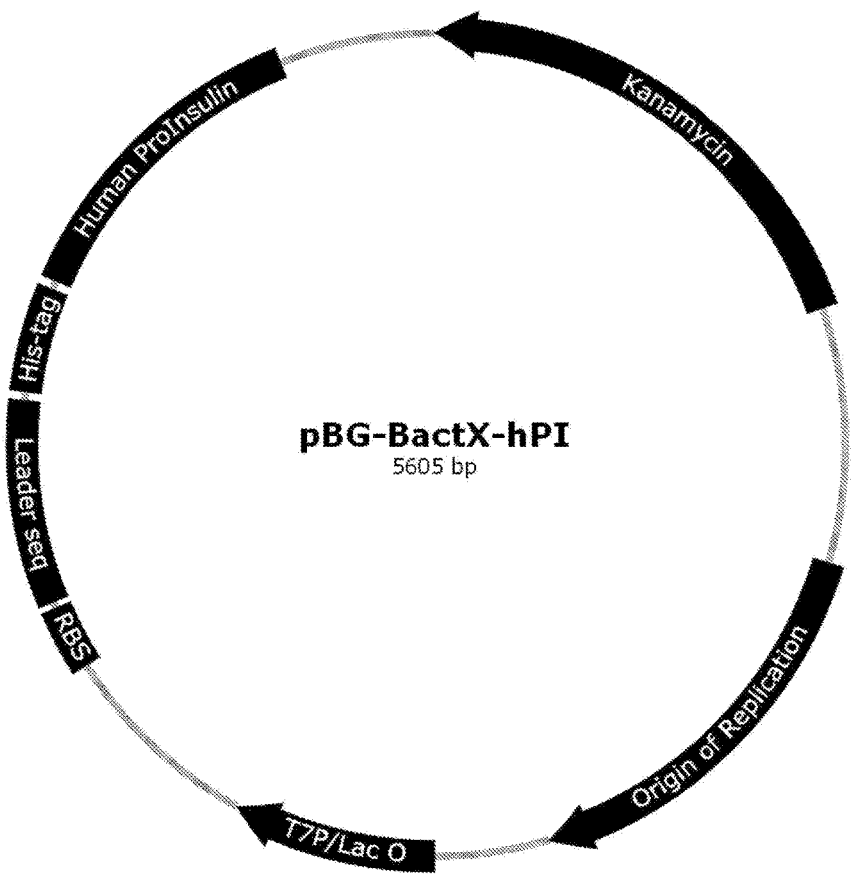
FIG. 1 illustrates an expression construct having a leader peptide for production of insulin in bacterial cells, according to an embodiment herein.

FIG. 1 illustrates an expression construct having a leader peptide, for production of insulin in bacterial cells, according to an embodiment herein. The expression construct includes a DNA sequence, of SEQ ID NO 2 encoding for the leader peptide of SEQ ID NO. 3. The expression construct further includes a DNA sequence encoding an affinity tag in the C-terminal end of the DNA sequence of the leader peptide. In one embodiment, the affinity tag is his-tag or a sequence with 6 histidines in succession. In a preferred embodiment, the DNA sequence encoding the affinity tag is ligated to the N-terminal end of the DNA sequence of, the leader peptide.

Further, the leader peptide DNA sequence with his-tag is ligated to DNA sequence encoding B-chain (for B-C-A conformation) or to DNA sequence encoding A-Chain (A-C-B conformation) of proinsulin via a DNA sequence encoding for arginine. In a preferred embodiment, the DNA sequence encoding for arginine is ligated to the DNA sequence of the leader peptide through the DNA sequence encoding the affinity tag.

The leader peptide of SEQ ID NO. 2 includes DNA sequence encoding for Methionine in its N-terminal end. The DNA sequence for Methionine is followed up by addition of DNA sequence encoding for glycine. The addition of glycine provides stability to the proinsulin-protein fusion. The proinsulin and leader peptide assembly enables single step digestion using Trypsin to separate insulin molecule from leader peptide and C-chain. Furthermore, there is no arginine in the leader peptide sequence.

The leader peptide of SEQ ID NO. 2 is a neutral peptide with nearly as many hydrophobic amino acids as hydrophilic amino acids. In one embodiment, the leader peptide has 49% amino acids as hydrophobic. The neutrality of the leader peptide enables increase in formation of stable proinsulin inclusion bodies when the expression construct of FIG. 1 is expressed in the bacterial cells. Further, inclusion of arginine as the cleavage site for removal of the leader peptide of SEQ ID NO 2 ensures that a single step is required to cleave off the C-chain and the leader peptide from the proinsulin fusion to obtain active insulin.

The DNA sequence for the protein of interest i.e. Insulin or its analogue is inserted in the Multiple Cloning Site (MCS) of the expression vector as shown in FIG. 1. Multiple cloning site or polylinker constitutes a short segment of DNA which contains a number of (generally up to 20) Restriction Enzyme (RE) sites—a standard feature of engineered plasmids.

In a preferred embodiment, the leader peptide and the MCS are custom synthesised as single stranded oligonucleotides, which are used for synthesis of double stranded DNA fragment by PCR. In one embodiment, the overlapping PCR method is used to synthesis double stranded DNA. Optionally, the leader peptide and the MCS may be directly synthesised as double stranded DNA fragments. Further, the RE sites were incorporated at 5' end and the 3' end of the synthesised DNA fragment. Furthermore, a Promoter/Operator region, a Ribosome Binding Site (RBS), an origin of replication and a antibiotic resistant gene were ligated with the PCR amplified DNA sequence coding for leader peptide, followed by MCS containing unique restriction enzyme sites. In one embodiment, the leader peptide is cloned downstream of the RBS, between Nco1 and EcoR1 restriction sites in the MCS.

Accordingly, the cleavage site, to cleave off the leader peptide and elicit a recombinant peptide/protein of interest, may be customised according to the recombinant peptide/protein of interest. The heterologous protein or the protein of interest may be cloned between any of the two RE sites in the MCS.

In an embodiment, the expression construct of FIG. 1 encodes a compound of Formula (I)

A-L-X-P in which, L is the leader peptide of SEQ ID NO 3, A is the affinity tag, X is the cleavage site and P is a heterologous protein. In another embodiment, the expression construct of Figure encodes a compound of Formula (II)

L-A-X-P

In another embodiment, the expression construct of FIG. 1 encodes a compound of formula (III):

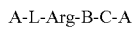
A-L-Arg-B-C-A

Or a compound of formula (IV):

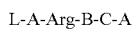
L-A-Arg-B-C-A in which, L is the leader peptide, A is a his-tag, acting as the affinity tag with six consecutive histidine residues, arginine is the cleavage site that links the leader peptide via the his-tag in its C-terminal end to the B chain of Proinsulin, whereas C is the C chain of Proinsulin and A is the A chain of Proinsulin. In one embodiment, the C-chain of Proinsulin includes an arginine residue only.

In another embodiment, the expression construct of FIG. 1 encodes a compound of formula (V):

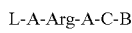
L-A-Arg-A-C-B

Or a compound of formula (VI):

A-L-Arg-A-C-B in which arginine, the cleavage site links the leader peptide via the his-tag in its C-terminal end to the A chain of Proinsulin.

In one embodiment, the leader peptide of SEQ ID NO 2 has first amino acid residue as methionine and the second amino acid residue as glycine, which imparts stability to the leader peptide. The advantage of having the arginine residue as the cleavage site to cleave off the leader peptide post-expression in the bacterial cells is that it enables single step, double reaction based enzymatic digestion of the compounds of formula I, II, III, IV, V or VI.

The embodiments above are further explained through way of examples as follows:

EXAMPLES

Example 1: Construction of Vector

The oligonucleotides for the human proinsulin (hPI) gene were custom synthesized (Sigma Aldrich). The single stranded oligonucleotides were reconstituted in 10 mM TE buffer (pH—8.0). The 0.5 uM of each forward and reverse oligonucleotide was used for PCR reaction to form double stranded DNA. The cycling conditions used for the PCR were: one cycle of 95° C. for 5 min for initial denaturation, followed by 35 cycles comprising of denaturation at 95° C. for 20 sec, annealing at 65° C. for 20 sec and elongation at 72° C. for 30 sec. The final extensions of 5 min at 72° C. were included for the complete synthesis of the gene. The series of sequential PCR reactions were carried out to synthesize the complete hPI gene. The EcoRI and XhoI restriction enzyme sites were incorporated at the 5' end and the 3' end of the hPI gene respectively in the final PCR amplification. The sequence ID of the vector synthesized herein is SEQ ID No 1.

Example 2: Purification of hPI Gene

The hPI (human proinsulin) gene was purified using phenol chloroform iso-amyl alcohol (25:24:1 ratio) extraction method and precipitated using ethanol. The pellet obtained was washed with 70% ethanol, air dried and reconstituted in 10 mM Tris buffer (pH 8.0).

Example 3: Cloning hPI Gene in the Vector 10 ug of the plasmid. DNA described herein and purified hPI gene were digested in 50 µl of reaction volume containing 1× restriction buffer with 10 Units each of EcoR I and Xho I (MBI Fermentas). The reaction was incubated for 30 min at 37° C. in the water bath. The digested plasmid DNA and hPI gene were purified using Qiagen gel Extraction Kit and the purified samples were eluted in 30 µl of elution buffer. The 10 µl ligation reactions were set using different vector to insert ratio and 4 Weiss units of T4 DNA ligase (MBI Fermentas). The ligation reaction were incubated at 4° C. for 16 hours and then transformed into DH5α strain of E. coli. The transformants were selected on Luria agar containing 75 µg/ml of Kanamycin. The sequence identity of the desired hPI gene is confirmed by nucleotide sequencing using automated DNA sequencer (CEQ 8000, Beckman Coulter).

Example 4: Transforming E. coli Cells

The vector-hPI DNA was transformed into E. coli expression host BL21 (DE3) and was allowed to grow in standard culture conditions. After the fermentation was completed, the inclusion bodies were isolated after lysing of cells. The inclusion bodies contained human pro-insulin in unfolded form.

Example 5: Isolation and Purification of Refolded Insulin from Human Proinsulin

Figure 2:
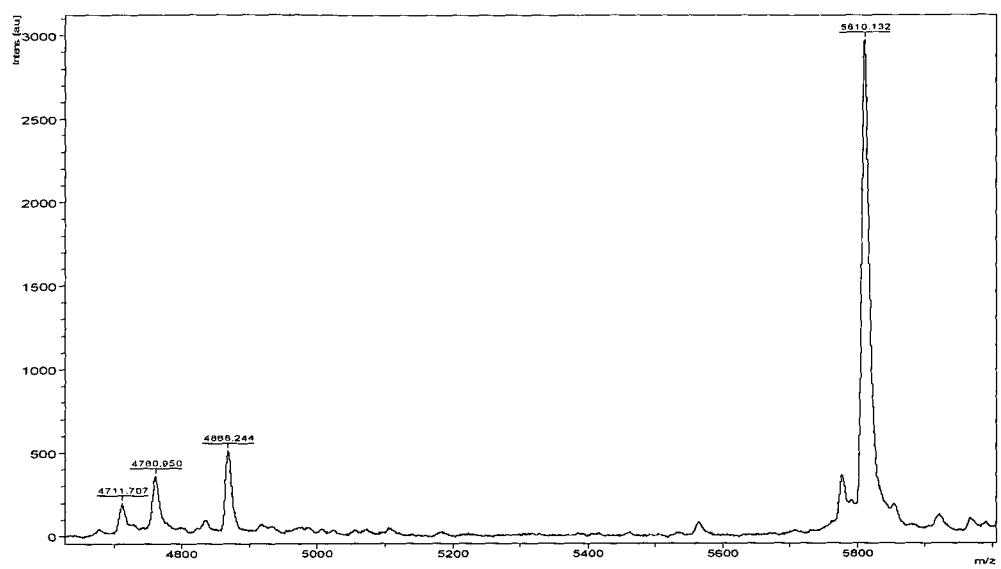
FIG. 2 illustrates MALDI-TOF spectrum obtained for Human Insulin and leader peptide obtained post enzymatic digestion of human Proinsulin, in accordance with the embodiments described herein.

The inclusion bodies having human proinsulin were further reduced and subjected to refolding using conventional methods in the presence of cysteine and cystine. The cysteine to cystine ratio was used in the ratio of 1:10. The refolding was performed at alkaline pH in the range of 8-10.5, preferably 9.5. The refolding reaction was incubated for 24 h at 4° C. The refolded. Proinsulin was converted to mature insulin by proteolysis using trypsin and Carboxypeptidase b with a ration of Proinsulin to enzyme of 300:1 and 600:1 (w/w), respectively. Digestion was performed in 0.1 M Tris/HCl, 1 mM $MgCl_2$, pH 7.5 at ambient temperature for 30 min. FIG. 2 illustrates MALDI-TOF spectrum obtained for Human Insulin and leader peptide obtained post enzymatic digestion of human Proinsulin, in accordance with the embodiments described herein. The peak of 5.8 kDa corresponds to Human Insulin and mass of 4.75 kDa corresponds to leader peptide. Hence, proving a single step digestion using the expression vector as described herein.

Example 6: Expression Analysis

SDS PAGE analysis of Human Insulin and Insulin analogues expressed from control vector and the vector described herein was performed. The reaction was run on 15% SDS-PAGE and stained with Coomassie brilliant blue.

Figure 3:
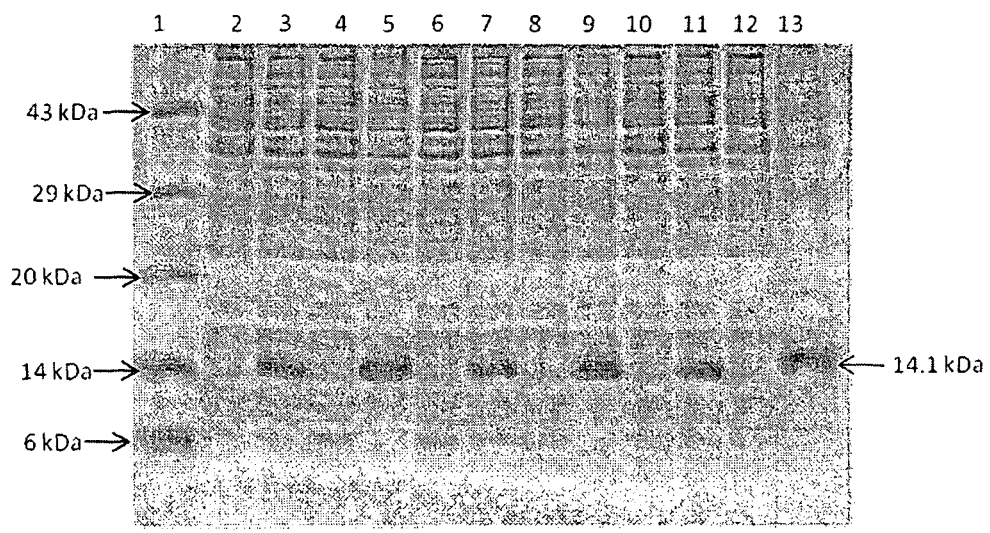
FIG. 3 illustrates SDS PAGE analysis of insulin and insulin analogues expressed in a control vector and in the vector of FIG. 1

FIG. 3 illustrates SDS PAGE analysis of insulin and insulin analogues expressed in a control vector and in the vector of FIG. 1. Lane 1 shows medium molecule weight marker, Lane2 shows Human Insulin uninduced sample from control vector, Lane 3 shows Human Insulin expressed from control vector, Lane 4 shows Human Insulin uninduced sample from the vector described herein, Lane 5 shows Human Insulin expressed from the vector described herein, Lane 6 shows Insulin Aspart uninduced sample from control vector, Lane 7 shows Insulin Aspart expressed from control vector, Lane 8 shows Insulin Aspart uninduced sample from the vector described herein, Lane 9 shows Insulin Aspart expressed from the vector described herein, Lane 10 shows Insulin Lispro uninduced sample from control vector, Lane 11 shows Insulin Lispro expressed from control vector, Lane 12 shows Insulin Lispro uninduced sample from the vector described herein, Lane 13 shows Insulin Lispro expressed from the vector described herein.

We claim:

1. A process for production of an insulin or insulin analogue, the process comprising expressing the insulin or insulin analogue through an expression vector in bacteria, wherein said expression vector comprises:
   a first nucleotide sequence encoding a leader peptide of SEQ ID NO:3;
   a second nucleotide sequence encoding an affinity tag, wherein the affinity tag is expressed linked to a C-terminal end or N-terminal end of said leader peptide; and
   a third nucleotide sequence encoding a cleavage site, wherein the third nucleotide sequence is ligated to the first nucleotide sequence encoding said leader peptide or to the second nucleotide sequence encoding said affinity tag.

2. The process of claim 1, wherein said leader peptide is expressed as a fusion protein; said fusion protein comprising fusion of said leader peptide of SEQ ID NO:3 and the insulin or inulin analogue.

3. The process of claim 1, wherein said bacteria are *E. coli*.

4. The process of claim 1, wherein said leader peptide has Methionine at N-terminus, followed by glycine.

5. The process of claim 1, wherein said affinity tag is his-tag.

6. The process of claim 1, wherein said cleavage site is arginine.

7. The process of claim 1, wherein said expression vector further comprises a multiple cloning site (MCS) in upstream region of said first nucleotide sequence encoding said leader peptide; a fourth nucleotide sequence encoding a ribosome binding site (RBS); a promoter or operator sequence downstream of the fourth nucleotide sequence encoding said ribosome binding site; and a fifth nucleotide sequence encoding an antibiotic selection marker in upstream region of said promoter or operator sequence.

8. The process of claim 7, wherein said antibiotic selection marker is kanamycin.

9. The process of claim 6, wherein the insulin or insulin analogue is expressed as a compound of formula: A-L-Arg-B-A-C, L-A-Arg-B-A-C, L-A-Arg-A-C-B or A-L-Arg-A-C-B; wherein A is said affinity tag, L is said leader peptide of SEQ ID NO 3, Arg is arginine, B is B-chain of Proinsulin or Proinsulin analogue, A is A-chain of Proinsulin or Proinsulin Analogue, C is C-chain of Proinsulin or Proinsulin Analogue.

10. The process of claim 9 further comprising digesting said compound with Trypsin to cleave off said leader peptide with affinity tag and C-chain of proinsulin to obtain molecule of insulin or insulin analogues having B-chain and A-Chain.

11. The process of claim 1, wherein said expression vector comprises nucleotide sequence of SEQ ID NO 1.

12. A process for production of a insulin or insulin analogue, the process comprising expressing the insulin or insulin analogue through an expression vector in bacteria, wherein said expression vector comprises:
 a first nucleotide sequence encoding a leader peptide of SEQ ID NO:3;
 a second nucleotide sequence encoding an affinity tag, wherein the affinity tag is expressed linked to a C-terminal end or a N-terminal end of said leader peptide;
 a third nucleotide sequence, wherein the third nucleotide sequence encodes a cleavage site or is a Restriction Enzyme (RE) site, and wherein the third nucleotide sequence is ligated to the first nucleotide sequence of encoding said leader peptide or to the second nucleotide sequence encoding said affinity tag;
 a multiple cloning site (MCS) in upstream region of the first nucleotide sequence encoding said leader peptide;
 a fourth nucleotide sequence encoding a ribosome binding site (RBS);
 a promoter or operator sequence downstream of the fourth nucleotide sequence encoding said ribosome binding site (RBS); and
 a fifth nucleotide sequence encoding an antibiotic selection marker, wherein the fifth nucleotide sequence is upstream of said promotor or operator sequence.

13. The process of claim 12, wherein said affinity tag is his-tag.

14. The process of claim 12, wherein said cleavage site is arginine.

15. A process for production of an insulin or insulin analogue, the process comprising expressing the insulin or insulin analogue through an expression vector in bacteria, wherein said expression vector comprises SEQ ID NO: 1.

16. The process of claim 15, wherein the bacteria are *E. coli*.

* * * * *